United States Patent [19]

Goldenberg et al.

[11] Patent Number: 5,834,440
[45] Date of Patent: Nov. 10, 1998

[54] RIBOZYME THERAPY FOR THE INHIBITION OF RESTENOSIS

[75] Inventors: Tsvi Goldenberg, La Jolla; Richard Tritz, San Diego, both of Calif.

[73] Assignee: Immusol Incorporated, San Diego, Calif.

[21] Appl. No.: 527,060

[22] Filed: Sep. 12, 1995

Related U.S. Application Data

[63] Continuation-in-part of Ser. No. 207,649, Mar. 7, 1994, abandoned.

[51] Int. Cl.$^6$ .......................... A61K 48/00; C07H 21/04; C12N 15/85; C12Q 1/68
[52] U.S. Cl. ............................ 514/44; 435/6; 435/91.31; 435/172.3; 435/320.1; 435/325; 435/366; 435/371; 435/375; 536/23.1; 536/23.2; 536/24.5
[58] Field of Search ......................... 435/6, 91.31, 172.1, 435/172.3, 320.1, 240.1, 240.2, 375; 536/23.1, 23.2, 24.5; 514/44

[56] References Cited

U.S. PATENT DOCUMENTS

| 4,987,071 | 1/1991 | Cech et al. | 435/91.31 |
| 5,225,347 | 7/1993 | Goldberg et al. | 435/320.1 |
| 5,254,678 | 10/1993 | Haseloff et al. | 536/23.2 |

FOREIGN PATENT DOCUMENTS

| 360 257 A2 | 3/1990 | European Pat. Off. . |
| WO 91/15580 | 10/1991 | WIPO . |
| WO 91/18012 | 11/1991 | WIPO . |
| WO 92/00990 | 1/1992 | WIPO . |
| WO 92/01786 | 2/1992 | WIPO . |
| WO 92/17206 | 10/1992 | WIPO . |
| WO 93/20691 | 10/1993 | WIPO . |
| WO 93/23057 | 11/1993 | WIPO . |
| WO 93/23569 | 11/1993 | WIPO . |
| 9402595 | 2/1994 | WIPO . |
| WO 94/02595 | 2/1994 | WIPO . |
| WO 95/13379 | 5/1995 | WIPO . |
| WO 95/23225 | 8/1995 | WIPO . |
| WO 9524202 | 9/1995 | WIPO . |
| WO 95/31541 | 11/1995 | WIPO . |
| WO 96/02651 | 2/1996 | WIPO . |

OTHER PUBLICATIONS

Dev et al., "Ribozymes to Cell Division Cycle (CDC–2) Kinase and Proliferating Cell Nuclear Antigen (PCNA) Prevent Intimal Hyperplasia in Rat Carotid Artery," *Circulation* 92(No. 8 suppl 1): 34, 1995.

Drenser et al., "Control of Gene Expression in Yeast Using Hairpin Ribozymes," *Protein Eng.* 8(suppl): 88, 1995.

Jarvis et al., "Inhibition of Vascular Smooth Muscle Cell Proliferation by Hammerhead Ribozymes Targeting c–myb," *Journal of Cellular Biochemistry Supplement 19A*: 221, 1995.

Mann et al., "Genetic engineering of vein grafts resistant to atherosclerosis," *Proc. Natl. Acad. Sci. USA* 92: 4502–4506, 1995.

Stinchcomb et al., "Towards the Application of Ribozymes to Human Health," *Journal of Cellular Biochemistry Supplement 19A*: 202, 1995.

Pines, J., "Protein kinases and cell cycle control," *Seminars in Cell Biology* 5: 399–408, 1994.

Charollais et al., "Into and out or G1: The control of cell proliferation," *Biochimie* 76: 887–894, 1994.

Pines, J., "Cyclins, CDKs and cancer," *Seminars in Cancer Biology* 6: 63–72, 1995.

Graña and Reddy, "Cell cycle control in mammalian cells: role of cyclins, cyclin dependent kinases (CDKs), growth suppressor genes and cyclin–dependent kinase inhibitors (CKIs)," *Oncogene* 11: 211–219, 1995.

Jaskulski et al., "Inhibition of Cellular Proliferation by Antisense Oligodeoxynucleotides to PCNA Cyclin," *Science* 240: 1544–1546, 1988.

Nikol et al., "Molecular biology an post–angioplasty restenosis," *Atherosclerosis* 123: 17–31, 1996.

Isner et al., "Arterial Gene Therapy for Restenosis," *Human Gene Therapy* 7: 989–1011, 1996.

Haber, E., "Can a Viral Serine Proteinase Inhibitor Prevent Postangioplasty Restenosis?" *Circulation* 94: 2694–2695, 1996.

Nakamura et al., "Passivation Reduces Restenosis After Coronary Angioplasty of High Grade Stenotic Lesions: Results of SHIPS (SHIga Pravastatin Study),", *Cardiovascular Drugs and Therapy* 10(4): 475–483, 1996.

Itoh et al., "Arterial Natriuretic Polypeptide inhibits Hypertrophy of Vascular Smooth Muscle Cells," *J. Clin. Invest.* 86: 1690–1697, 1990.

Bravo, R., "Synthesis of the Nuclear Protein Cyclin (PCNA) and Its Relationship with DNA Replication," *Experimental Cell Research* 163: 289–293, 1986.

Pickering et al., "Proliferative Activity in Peripheral and Coronary Atherosclerosis Plaque among Patients Undergoing Percutaneous Revascularization," *J. Clin. Invest.* 91: 1469–1480, 1993.

Bennett and Schwartz, "Antisense Therapy for Angioplasty Restenosis. Some Critical Considerations," *Circulation* 92: 1981–1993, 1995.

Mattsson and Clowes, "Current Concepts in Restenosis Following Balloon Angioplasty," *Trends in Cardiovasc. Med.* 5: 200–204, 1995.

Almendral et al., "Cloning and sequence of the human nuclear protein cyclin: Homology with DNA–binding proteins," *Proc. Natl. Acad. Sci. USA* 84: 1575–1579, 1987.

Pines, J., "The cell cycle kinases," *Seminars in Cancer Biology* 5: 305–313, 1994.

(List continued on next page.)

Primary Examiner—John L. LeGuyader
Attorney, Agent, or Firm—Seed and Berry LLP

[57] ABSTRACT

As an effective therapy for restenosis, this invention provides ribozymes and ribozyme delivery systems useful to inhibit abnormal smooth muscle cell proliferation in vascular tissue. Methods of producing ribozymes and gene therapy utilizing these ribozymes also are provided.

22 Claims, 4 Drawing Sheets

OTHER PUBLICATIONS

Liu et al., "Cationic Liposome–mediated Intravenous Gene Delivery," *Journal of Biological Chemistry* 270(42):24864–24870, 1995.

Guzman et al., "In vivo suppression of injury–induced vascular smooth muscle cell accumulation using adenovirus–mediated transfer of the herpes simplex virus thymidine kinase gene," *Proc. Natl. Acad. Sci. USA 91*: 10732–10736, 1994.

French et al., "Percutaneous Transluminal In Vivo Gene Transfer by Recombinant Adenovirus in Normal Porcine Coronary Arteries, Atherosclerosis Arteries, and Two Models of Coronary Restenosis," *Circulation 90*: 2402–2413, 1994.

Libby et al., "A Cascade Model for Restenosis: A Special Case of Atheresclerosis Progression," *Circulation 86*(suppl III): III–47–III–52, 1992.

Lincoff et al., "Local Drug Delivery for the Prevention of Restenosis. Fact, Fancy, and Future," *Circulation 90*(4): 2070–2084, 1994.

Mann et al., "Genetic engineering of vein grafts resistant to atherosclerosis," *Proc. Natl. Acad. Sci. USA 92*: 4502–4506, 1995.

Epstein et al., "Do Antisense Approaches to the Problem of Restenosis Make Sense?" *Circulation 88*(3): 1351–1353, 1993.

Landau et al., "Percutaneous Transluminal Coronary Angioplasty," *The New England Journal of Medicine 330*(14): 981–983, 1994.

Simons et al., "Antisense c–myb oligonucleotides inhibit intimal arterial smooth muscle cell accumulation in vivo," *Nature 359*: 67–70, 1992.

Waksman et al., "Endovascular Low–Dose Irradiation Inhibits Neointima Formation After Coronary Artery Balloon Injury in Swine. A Possible Role for Radiation Therapy in Restenosis Prevention," *Circulation 91*: 1533–1539, 1995.

Snyder et al., "Ribozyme–Mediated Inhibition of bcr–abl Gene Expression in a Philadelphia Chromosome–Positive Cell Line," *Blood 82*(2): 600–605, 1993.

Morishita et al., "Single intraluminal delivery of antisense cdc2 kinase and proliferating–cell nuclear antigen oligonucleotides results in chronic inhibition of neoimtimal hyperplasia," *Proc. Natl. Acad. Sci. USA 90*: 8474–8478, 1993.

Jaskulski et al., "Regulation of the Proliferation Cell Nuclear Antigen Cyclin and Thymidine Kinase mRNA Levels by Growth Factors," *Journal of Biological Chemistry 263*(21): 10175–10179, 1988.

Travali et al., "Structure of the Human Gene for the Proliferating Cell Nuclear Antigen," *Journal of Biological Chemistry 264*(13): 7466–7472, 1989.

Bravo et al, "Changes in the nuclear distribution of cyclin (PCNA) but not its synthesis depend on DNA replication," *EMBO Journal 4*(3): 655–661, 1985.

Morris and Mathews, "Regulation of Proliferating Cell Nuclear Antigens during the Cell Cycle," *Journal of Biological Chemistry 264*(23): 13856–13864, 1989.

von der Leyen et al., "Gene therapy inhibiting neointimal vascular lesion: In vivo transfer of endothelial cells nitric oxide synthase gene," *Proc. Natl. Acad. Sci. USA 92*: 1137–1141, 1995.

Simari et al., "Regulation of Cellular Proliferation and Intimal Formation following Balloon injury in Atherosclerosis Rabbit Arteries," *J. Clin. Invest. 98*(1): 225–235, 1996.

Shimayama et al., "Nuclease–resistant chimeric ribozymes containing deoxyribonucleotides and phosphorothioate linkages," *Nucleic Acids Research 21*(11): 2605–2611, 1993.

Taylor et al., "Chimeric DNA–RNA hammerhead ribozymes have enhanced in vitro catalytic efficiency and increased stability in vivo," *Nucleic Acids Research 20*(17): 4559–4565, 1992.

Simons et al., "Antisense Proliferating Cell Nuclear Antigen Oligonucleotides Inhibit Intimal Hyperplasia in a Rat Carotid Artery Injury Model," *J. Clin. Invest. 93*: 2351–2356, 1994.

Guzman et al., "Efficient and Selective Adenovirus–Mediated Gene Transfer Into Vascular Neointima," *Circulation 88*: 2838–2848, 1993.

Steg et al., "Arterial Gene Transfer to Rabbit Endothelial and Smooth Muscle Cells Using Percutaneous Delivery of an Adenoviral Vector," *Circulation 90*: 1648–1656, 1994.

Nabel, E., "Gene Therapy for Cardiovascular Disease," *Circulation 91*(2): 541–548, 1995.

Barr et al. "Efficient catheter–mediated gene transfer in the heart using replication–defective adenovirus," *Gene Therapy 1*: 51–58, 1994.

Biro et al., "Inhibitory effects of antisense oligodeoxynucleotides targeting c–myc mRNA on smooth muscle cell proliferation and migration," *Proc. Natl. Acad. Sci. USA 90*: 654–658, 1993.

Chang et al., "Cytostatic Gene Therapy for Restenosis Using Adenovirus–Mediated Overexpression of the Cyclin/CDK Inhibitor, p21," *Circulation Supplement 92*(8): 747, abstract #3593, 1995.

Chatterjee et al., "Dual–Target Inhibition of HIV–1 in Vitro by Means of an Adeno–Associated Virus Antisense Vector," *Science 258*: 1485–1488, 1992.

Content and Mahieu, "Construction of a Ribozyme Cleaving Human IL–6 mRNA," *J. Cell. Biochem. Suppl.*(17 part B): abstract #E502, p. 110, 1993.

Cotten and Birnstiel, "Ribozyme mediated destruction of RNA in vivo," *The EMBO Journal 8*(12): 3861–3866, 1989.

Forster and Symons et al., "Self–Cleavage of Plus and Minus RNAs of a Virusoid and a Structural Model for the Active Sites," *Cell 49*: 211–220, 1987.

Fumato et al., "The Utility of an Antifos Ribozyme in Reversing Cisplatin Resistance in Human Carcinomas," *Advan. Enzyme Regul. 32*: 195–209, 1992.

Hampel et al., "'Hairpin' catalytic RNA model: evidence for helices and sequence requirement for substrate RNA," *Nucleic Acids Research 18*(2): 299–304, 1990.

Hanahan, D., "Studies on Transformation of *Escherichia coli* with Plasmids," *J. Mol. Biol. 166*: 557–580, 1983.

Haseloff and Gerlach, "Simple RNA enzymes with new and highly specific endoribonuclease activities," *Nature 334*: 585–591, 1988.

Letsinger et al., "Cholesteryl–conjugated oligonucleotides: Synthesis, properties, and activity as inhibitors of replication of human immunodeficiency virus in cell culture," *Proc. Natl. Acad. Sci. USA 86*: 6553–6556, 1989.

Lever et al., "Identification of a Sequence Required for Efficient Packaging of Human Immunodeficiency Virus Type 1 RNA into Virions," *Journal of Virology 63*(9): 4085–4087, 1989.

Llewellyn et al., "Structure and Expression of an Alcohol Dehydrogenase 1 Gene from *Pisum sativum* (cv. Greenfeast)," *J. Mol. Biol. 195*: 115–123, 1987.

Mahieu and Content, "Construction of a Ribozyme Cleaving Human IL–6 mRNA," *Journal of Interferon Research* 12(suppl. 1): abstract #P4–6, p. S79, 1992.

Morishita et al., "Single intraluminal delivery of antisense cdc2 kinase and proliferating–cell nuclear antigen oligonucleotides results in chronic inhibition of neointimal hyperplasia," *Proc. Natl. Acad. Sci. USA 90*: 8474–8478, 1993.

Myers et al., "Restenosis is associated with decreased coronary artery nitric oxide synthase," *International Journal of Cardiology 55*: 183–191, 1996.

Narayan et al., "Nuclease Resistant Ribozymes Against Hepatitis B Surface Antigen mRNA," *J. Cell. Biochem. Suppl.* (17 Part E): 213, abstract #S411, 1993.

Pace et al., "Construction of Ribozymes Which Discriminate Between Closely Related mRNAs," *J. Cel. Biochem. Suppl.* (17 Part E): 213, abstract #S412, 1993.

Rossi et al., "The Potential Use of Catalytic RNAs in Therapy of HIV Infection and Other Diseases," *Pharmac. Ther. 50*: 245–254, 1991.

Scanlon et al., "Development of a c–fos ribozyme to circumvent cisplatin resistance in human ovarian carcinoma cells," *Proc. Am. Assoc. Cancer Annu. Meet. 31*: abstract #2399, p. 404, 1990.

Scanlon et al., "Ribozyme–mediated cleavage of c–fos mRNA reduces gene expression of DNA synthesis enzymes and metallothionein," *Proc. Natl. Acad. Sci. USA 88*: 10591–10595, 1991.

Simons et al., "Antisense c–myb oligonucleotides suppress smooth muscle proliferation in a rat model of restenosis," *Circulation 86*(4): abstract #899, p. I–227, 1992.

Sioud, M., "Interaction Between Tumour Necrosis Factor α Ribozyme and Cellular Proteins. Involvement in Ribozyme Stability and Activity," *J. Mol. Biol. 242*: 619–629, 1994.

Sullenger and Cech, "The Importance of Colocalization of Ribozyme and Substrate Containing RNAs for Trans Cleavage in Vivo," *J. Cell. Biochem. Suppl.* (17 Part E): 209, abstract #S316, 1993.

von der Leyen et al., "Gene therapy inhibiting neointimal vascular lesion: In vivo transfer of endothelial cell nitric oxide synthase gene," *Proc. Natl. Acad. Sci USA 92*: 1137–1141, 1995.

Walbot and Bruening, "Plant development and ribozymes for pathogens," *Nature 334*: 196–197, 1988.

Weizsäecker et al., "Ribozymes Mediated Cleavage of Hepatitis B and Duck Hepatitis B Virus RNA," *American Association for the Study of Liver Diseases, Postgraduate Course & 43rd Annual Meeting,* Chicago, Oct. 31–Nov. 3, 1992, p. 88A, Abstract #175.

Scanlon et al PNAS 88: 10591–10595, 1991.

Chatterjee et al. Science 258: 1485–1488 (1992).

Stull et al. Pharm. Res. 12: 465–483 (1995).

RIBOZYME THERAPY FOR THE INHIBITION OF RESTENOSIS

CROSS-REFERENCE TO RELATED APPLICATIONS

This application is a continuation-in-part of U.S. application Ser. No. 08/207,649 filed Mar. 7, 1994, now abandoned, which application is incorporated by reference herein.

TECHNICAL FIELD

The present invention relates generally to therapeutics, and more specifically, to compositions and methods which may be utilized in the treatment and/or prevention of restenosis.

BACKGROUND OF THE INVENTION

In 1992, an excess of 300,000 angioplasties were performed in the United States. Restenosis is a major complication following angioplasty, occurring in 30%–60% of patients. Indeed, restenosis is the single most significant problem in interventional cardiology and costs the health care system in excess of $1 billion per year.

Restenosis following angioplasty is the result of local vascular injury, and is characterized by the local infiltration of platelets and macrophages, and local activation of the clotting system. These factors result in the elaboration of a number of biologic mediators of smooth muscle cell (SMC) migration and proliferation. These SMCs migrate into the vascular intima and begin to proliferate and produce extracellular matrix (ECM), resulting in the formation of a fibrocellular mass which can obstruct blood flow. Further, injury has been shown to induce the expression of a variety of oncogenes that are believed to play a role in the cellular response to this injury. Thus, a need exists for an effective therapy to prevent and treat restenosis. The present invention satisfies this need and further provides other, related, advantages as well.

SUMMARY OF THE INVENTION

As an effective therapy for restenosis, this invention provides ribozymes and ribozyme delivery systems useful to inhibit abnormal smooth muscle cell proliferation in vascular tissue. Methods of producing ribozymes and gene therapy utilizing these ribozymes also are provided.

Accordingly, in one aspect the present invention ribozymes having the ability to inhibit abnormal smooth muscle cell proliferation in vascular tissue. Preferably, the ribozyme is a hammerhead or hairpin ribozyme, representative examples of which recognize the target site sequences set forth below and in the Examples. In preferred embodiments, the present invention also provides nucleic acid molecule encoding such ribozymes; further preferably, the nucleic acid is DNA or cDNA. Even further preferably, the nucleic acid molecule is under the control of a promoter to transcribe the nucleic acid.

In another aspect, the present invention provides host cells containing the ribozymes described herein, vectors comprising the nucleic acid encoding the ribozymes described herein, and host cells comprising such a vector. Preferably, the vector is a plasmid, a virus, retrotransposon, a cosmid or a retrovirus. In one embodiment where the vector is a retroviral vector, the nucleic acid molecule encoding the ribozyme under the control of a promoter, which is preferably a pol III promoter, further preferably a human tRNA$^{val}$ promoter or an adenovirus VA1 promoter, is inserted between the 5' and 3' long terminal repeat sequences of the retrovirus.

The present invention also provides a host cell stably transformed with such a retroviral vector. Preferably, the host cell is a murine or a human cell.

In a further aspect, the present invention provides methods for producing a ribozyme, the ribozyme being able to inhibit abnormal smooth muscle cell proliferation in vascular tissue, which method comprises providing a nucleic acid molecule (e.g., DNA) encoding the ribozyme under the transcriptional control of a promoter, and transcribing the nucleic acid molecule to produce the ribozyme. Preferably, the method further comprises purifying the ribozyme produced. The ribozyme may be produced in vitro, in vivo or ex vivo.

In yet another aspect, the present invention provides methods of inhibiting abnormal smooth muscle cell proliferation in vascular tissue, which method comprises introducing into the cell an effective amount of the ribozymes described herein. In one embodiment, such methods comprise introducing into the cell an effective amount of DNA encoding a ribozyme as described herein and transcribing the DNA to produce the ribozyme. Preferably, the cell is a human cell.

In still a further aspect, the present invention provides methods of preventing abnormal smooth muscle cell proliferation in vascular tissue, which methods comprise introducing into the cell an effective amount of a nucleic acid molecule (e.g., DNA) encoding a ribozyme as described herein and transcribing the DNA to produce the ribozyme. Preferably, the cell is a human cell.

In preferred embodiments, the methods further comprise administering the cell transduced with a retroviral vector to a mammal of the same species as that from which the transduced cell was obtained. In other preferred embodiments, the cell transduced with the retroviral vector has been obtained from the mammal receiving the transduced cell.

These and other aspects of the present invention will become evident upon reference to the following detailed description and attached drawings. In addition, various references are set forth herein that describe in more detail certain procedures or compositions (e.g., plasmids, etc.), and are therefore incorporated by reference in their entirety as if each were individually noted for incorporation.

DETAILED DESCRIPTION OF THE INVENTION

Restenosis is a major clinical problem and as the result of a need for repeat hospitalization, repeat angioplasty or bypass surgery, restenosis costs the nation's health care system in excess of $1 billion per year. Restenosis is believed to comprise three important components. First, myointimal proliferation of vascular smooth muscle cells and the subsequent deposition of ECM results in a fibrocellular mass which can encroach upon the vascular lumen. Second, following acute angioplasty, there may be significant elastic recoil of the artery which contributes to a late loss of luminal dimension. Finally, platelets and thrombus adherent to the vascular wall may, over time, organize into a fibrocellular mass.

Smooth muscle cells (SMCs) are capable of producing and responding to a variety of growth factors including platelet-derived growth factor (PDGF), transforming growth factor (TGF), fibroblast growth factor (FGF), insulin-like growth factor (IGF), and interleukins. These same factors have been found in human restenotic lesions. In addition, a variety of oncogenes (e.g., c-myc, c-fos, and c-myb) have been found to be involved in smooth muscle cell migration and proliferation as well as deposition of ECM that is associated with post-vascular injury. Smooth muscle cells themselves are capable of regulating their own growth by local autocrine and paracrine mechanisms.

As discussed in more detail below, by interfering with the local production and action of the growth factors, oncogenes and cell regulatory proteins involved with SMC growth following vascular injury, restenosis can be effectively treated and/or prevented. This invention accomplishes such by providing ribozymes and methods of using ribozymes that directly block the production of the growth factors, oncogenes and cell regulatory proteins involved with SMC growth following vascular injury.

As used herein, "ribozymes" are intended to include RNA molecules that contain anti-sense sequences for specific recognition, and an RNA-cleaving enzymatic activity. The catalytic strand cleaves a specific site in a target RNA at greater than stoichiometric concentration. Two "types" of ribozymes are particularly useful in this invention, the hammerhead ribozyme (Rossi, J.J. et al., *Pharmac. Ther.* 50:245–254, 1991) and the hairpin ribozyme (Hampel et al., *Nucl. Acids Res.* 18:299–304, 1990, and U.S. Pat. No. 5,254,678, issued Oct. 19, 1993). Because both hammerhead and hairpin ribozymes are catalytic molecules having antisense and endoribonucleotidase activity, ribozyme technology has emerged as a potentially powerful extension of the antisense approach to gene inactivation. The ribozymes of the invention typically consist of RNA, but such ribozymes may also be composed of nucleic acid molecules comprising chimeric nucleic acid sequences (such as DNA/RNA sequences) and/or nucleic acid analogs (e.g., phosphorothioates).

Accordingly, within one aspect of the present invention ribozymes are provided which have the ability to inhibit pathologic smooth muscle proliferation and restenosis. Such ribozymes may be in the form of a "hammerhead" (for example, as described by Forster and Symons, *Cell* 48:211–220, 1987; Haseloff and Gerlach, *Nature* 328:596–600, 1988; Walbot and Bruening, *Nature* 334:196, 1988; Haseloff and Gerlach, *Nature* 334:585, 1988) or a "hairpin" (for example, as described by Haseloffet al., U.S. Pat. No. 5,254,678, issued Oct. 19, 1993 and Hempel et al., European Patent Publication No. 0 360 257, published Mar. 26, 1990), and have the ability to specifically target, cleave and inactivate factors responsible for restenosis. In one embodiment, the ribozyme has the ability to inhibit the activity of a growth factor responsible for abnormal smooth muscle cell proliferation in vascular tissue. Such rowth factors include, but are not limited to platelet derived growth factor, fibroblast growth factor, insulin-like growth factor, c-myc, c-myb, c-fos, cdc2 kinase, PCNA, Cyclin B1, Lysyl Oxidase, TGF-α, TGF-β, interleukin, and components of the extracellular matrix. As used herein, the term "abnormal smooth muscle cell proliferation" shall mean any small cell proliferation and deposition of extracellular matrix occurring in response to vascular injury or trauma involved by any angioplasty, stent, balloon angioplasty, atherectomy, laser surgery, endovascular or surgical procedure.

The sequence requirement for the hairpin ribozyme is any RNA sequence consisting of NNNBN*GUCNNNNNN (where N*G is the cleavage site, where B is any of G, C, or U, and where N is any of G, U, C, or A)(SEQ ID NO: 1). Representative examples of recognition or target sequences for hairpin ribozymes are set forth below in the Examples. The sequence requirement at the cleavage site for the hammerhead ribozyme is any RNA sequence consisting of NUX (where N is any of G, U, C, or A and X represents C, U, or A) can be targeted. Accordingly, the same target within the hairpin leader sequence, GUC, is useful for the hammerhead ribozyme. The additional nucleotides of the hammerhead ribozyme or hairpin ribozyme is determined by the target flanking nucleotides and the hammerhead consensus sequence (see Ruffner et al., *Biochemistry* 29:10695–10702, 1990).

This information, and the published sequence of nucleic acids coding for c-myc, c-myb, c-fos, cdc2 kinase (Genbank accession number Y00272; Lee and Nurse, *Nature* 327:31–35, 1987), proliferating cell nuclear antigen ("PCNA" Genbank accession number J04718; Travali et al., *G. Biol. Chem.* 264(13):7466–7472, 1989), Cyclin B1 (Genbank accession number M25753; Pines and Hunter, *Cell* 58:833–846, 1989), Lysyl Oxidase (Genbank accession number M94054), TGF-α and TGF-β proteins enables the production of the ribozymes of this invention. Appropriate base changes in the ribozyme is made to maintain the necessary base pairing with the target RNA sequences.

Cech et al. (U.S. Pat. No. 4,987,071, issued Jan. 22, 1991) has disclosed the preparation and use of certain synthetic ribozymes which have endoribonuclease activity. These ribozymes are based on the properties of the Tetrahymena ribosomal RNA self-splicing reaction and require an eight base pair target site. A temperature optimum of 50° C. is reported for the endoribonuclease activity. The fragments that arise from cleavage contain 5' phosphate and 3' hydroxyl groups and a free guanosine nucleotide added to the 5' end of the cleaved RNA. In contrast, the ribozymes of this invention hybridize efficiently to target sequences at physiological temperatures, making them suitable for use in vivo, not merely as research tools (see, column 15, lines 18–42, of Cech et al., U.S. Pat. No. 4,987,071).

The ribozymes of this invention, as well as DNA encoding such ribozymes and other suitable nucleic acid molecules, described in more detail below, can be chemically synthesized using methods well known in the art for the synthesis of nucleic acid molecules. Alternatively, Promega, Madison, Wis., USA, provides a series of protocols suitable for the production of RNA molecules such as ribozymes. The ribozymes also can be prepared from a DNA molecule or other nucleic acid molecule (which, upon transcription, yields an RNA molecule) operably linked to an RNA polymerase promoter, e.g., the promoter for T7 RNA polymerase or SP6 RNA polymerase. Such a construct may be referred to as a vector. Accordingly, also provided by this invention are nucleic acid molecules, e.g., DNA or cDNA, coding for the ribozymes of this invention. When the vector also contains an RNA polymerase promoter operably linked to the DNA molecule, the ribozyme can be produced in vitro upon incubation with the RNA polymerase and appropriate nucleotides. In a separate embodiment, the DNA may be inserted into an expression cassette, such as described in Cotten and Birnstiel, *EMBO J* 8(12):3861–3866, 1989, and in Hempel et al., *Biochemistry* 28:4929–4933, 1989. A more detailed discussion of molecular biology methodology is disclosed in Sambrook et al., *Molecular Cloning: A Laboratory Manual*, Cold Spring Harbor Press, 1989.

After synthesis, the ribozyme can be modified by ligation to a DNA molecule having the ability to stabilize the ribozyme and make it resistant to RNase. Alternatively, the ribozyme can be modified to the phosphothio analog for use in liposome delivery systems. This modification also renders the ribozyme resistant to endonuclease activity.

The ribozyme molecule also can be in a host procaryotic or eukaryotic cell in culture or in the cells of an organism. Appropriate procaryotic and eukaryotic cells can be transfected with an appropriate transfer vector containing the DNA molecule encoding a ribozyme of this invention. Alternatively, the ribozyme molecule, including nucleic acid molecules encoding the ribozyme, may be introduced into the host cell using traditional methods such as transformation using calcium phosphate precipitation (Dubensky et al., *PNAS* 81:7529–7533, 1984), direct microinjection of such nucleic acid molecules into intact target cells (Acsadi et al., *Nature* 352:815–818, 1991), and electroporation whereby cells suspended in a conducting solution are subjected to an intense electric field in order to transiently polarize the membrane, allowing entry of the nucleic acid molecules. Other procedures include the use of nucleic acid molecules linked to an inactive adenovirus (Cotton et al., *PNAS* 89:6094, 1990), lipofection (Felgner et al., *Proc. Natl. Acad. Sci. USA* 84:7413–7417, 1989), microprojectile ombardment (Williams et al., *PNAS* 88:2726–2730, 1991), polycation compounds such as polylysine, receptor specific ligands, liposomes entrapping the nucleic acid molecules, spheroplast fusion whereby *E coli* containing the nucleic acid molecules are stripped of their outer cell walls and fused to animal cells using polyethylene glycol, viral transduction, (Cline et al., *Pharmac. Ther.* 29:69, 1985; and Friedmann et al., *Science* 244:1275, 1989), and DNA ligand (Wu et al, *J. of Biol. Chem.* 264:16985–16987, 1989), as well as psoralen inactivated viruses such as Sendai or Adenovirus. In a preferred embodiment, the ribozyme is introduced into the host cell utilizing a liposome.

When the DNA molecule is operatively linked to a promoter for RNA transcription, the RNA can be produced in the host cell when the host cell is grown under suitable conditions favoring transcription of the DNA molecule. The vector can be, but is not limited to a plasmid, a virus, a retrotransposon or a cosmid. Examples of such vectors are disclosed in U.S. Pat. No. 5,166,320. Other representative vectors include adenoviral vectors (e.g., WO 94/26914, WO 93/9191; Kolls et al., *PNAS* 91(1):215–219, 1994; Kass-Eisler et al., *PNAS* 90(24):11498–502, 1993; Guzman et al., *Circulation* 88(6):2838–48, 1993; Guzman et al., *Cir. Res.* 73(6):1202–1207, 1993; Zabner et al., *Cell* 75(2):207–216, 1993; Li et al., *Huim Gene Ther.* 4(4):403–409, 1993; Caillaud et al., *Eur. J Neurosci.* 5(10):1287–1291, 1993), adeno-associated vector type 1 ("AAV-1") or adeno-associated vector type 2 ("AAV-2") (see WO 95/13365; Flotte et al., *PNAS* 90(22):10613–10617, 1993), retroviral vectors (e.g., EP 0 415 731; WO 90/07936; WO 91/02805; WO 94/03622; WO 93/25698; WO 93/25234; U.S. Pat. No. 5,219,740; WO 93/11230; WO 93/10218) and herpes viral vectors (e.g., U.S. Pat. No. 5,288,641). Methods of utilizing such vectors in gene therapy are well known in the art, see, for example, Larrick, J.W. and Burck, K.L., *Gene Therapy: Application of Molecular Biology*, Elsevier Science Publishing Co., Inc., New York, New York, 1991 and Kreigler, M., *Gene Transfer and Expression: A Laboratory Manual*, W.H. Freeman and Company, New York, 1990.

To produce ribozymes in vivo utilizing vectors, the nucleotide sequences coding for ribozymes are preferably placed under the control of a strong promoter such as the lac, SV40 late, SV40 early, or lambda promoters. Ribozymes are then produced directly from the transfer vector in vivo.

As noted above, within one embodiment the viral vector is a retrovirus, such as a non-virulent vaccinia based viral vector, a Moloney murine leukemia virus, or an HIV vector as described in Lever, A., *J Virol.* 63:4085–4087, 1989. Retroviral vectors are particularly useful for gene therapy of restenosis. An appropriate retroviral vector for such gene therapy is a retrovirus having a foreign nucleic acid (DNA or cDNA) sequence inserted between the 5' and 3' long terminal repeat (LTR) regions of he retrovirus. The foreign nucleic acid sequence is under the control of a promoter, for example, the retroviral LTR or an inserted pol III promoter such as the human tRNA$^{Val}$ promoter or the adenovirus VAl promoter. The retroviral vector then stably expresses the ribozyme in the host cell.

Further provided by this invention are retroviral vectors having inserted between the 5' and 3' LTR more than one nucleic acid molecule encoding a ribozyme of this invention, each molecule under the control of a separate pol III promoter or alternatively, under the control of single pol III promoter or the retroviral LTR. These retroviral vectors provide the advantage of providing multi-functional therapy against restenosis, each specific therapy working in synergy. In addition, because only a limited number of vectors are used, the number of integration sites in the host cell are reduced thereby reducing the possibility of activation of host cellular DNA sequences by the inserted retroviral vector.

Host procaryotic and eucaryotic cells stably transduced with the vectors described above also are provided by this invention. Suitable host cells include bacterial cells, mouse cells, rat cells, mouse cells, and human cells, for example, vascular smooth muscle cells.

Methods of inhibiting abnormal smooth cell vascular tissue proliferation or restenosis are also provided by this invention. Such methods require contacting a suitable cell or tissue with an effective amount ribozyme of this invention or alternatively, by transducing the cell with an effective amount vector having a nucleic acid molecule encoding the ribozyme. Effective amounts are easily determined by those of skill in the art using well known methodology. When exogenously delivering the ribozyme, the nucleic acid molecule can be embedded within a stable RNA molecule or in another form of protective environment, such as a liposome. Alternatively, the RNA can be embedded within RNase resistant DNA counterparts. Cellular uptake of the exogenous ribozyme can be enhanced by attaching chemical groups to the DNA ends, such as cholesteryl moieties (Letsinger et al., *P.N.A.,S., U.S.A.* 1989).

In another aspect of the invention, target cells are transduced under conditions favoring insertion of the vector into the target cell and stable expression of the nucleic acid encoding the specific ribozyme. The target cell can include but is not limited to a vascular smooth muscle cell or a cell responsible for the deposition of proteins involved in the formation of extracellular matrix. Such cells are well known to those of skill in the art.

Accordingly, another aspect of this invention provides methods for interfering with or preventing abnormal smooth muscle proliferation in a suitable cell, by reacting the target RNA sequence with a ribozyme of this invention. Within the cell or within the cells of an organism, a transfer vector as described above encoding one or more ribozymes is transfected into a cell or cells using methods described in Llewwllyn et al., (1987) *J Mol. Biol.* 195:115–123 and Hanahan et al. (1983) 166:557–580, each incorporated herein by reference. Inside the cell, the transfer vector replicates and the DNA coding for the ribozyme is transcribed by cellular polymerases to produce ribozymes which then inactivate factors responsible for abnormal smooth muscle cell proliferation, abnormal extracellular matrix deposition and restenosis. Micromanipulation techniques such as microinjection also can be used to insert the vector into the cell so that the transfer vector or a part thereof is integrated into the genome of the cell. Transcription of the integrated material gives rise to ribozymes which then inactivate the target proteins. As used herein, the term "inactivate" is intended to mean interfere with the production of the protein products such as those discussed above (e.g., c-myc or TGF-β).

Compositions also are provided by this invention. These compositions contain any of the above described ribozymes, DNA molecules, vectors or host cells. In one aspect of this invention, the compositions also contain a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents.

Host cells containing the ribozymes, nucleic acids and/or vectors described above also are within the scope of this invention. These host cells can be procaryotic cells, for example bacterial cells or eucaryotic cells, such as mammalian, human, rat, or mouse cells. The host cells transduced with nucleic acids encoding the ribozymes are useful to recombinantly produce the ribozymes. Thus, also provided by this invention is a method for producing a ribozyme, in vitro or in vivo, the ribozyme being able to inhibit abnormal smooth muscle cell proliferation in vascular tissue. DNA encoding the ribozyme is provided to the cell, the DNA being under the transcriptional control of a promoter, using methods well known to those of skill in the art. See Sambrook et al., *Molecular Cloning: A Laboratory Manual,* Cold Spring Harbor Laboratory (1989), incorporated herein by reference. The DNA is then transcribed in the cell to produce the ribozyme. When produced in vitro, the ribozyme can be purified or isolated from the cell by using methods well known in the art. The DNA can be transferred in a carrier or in a vector in a carrier a number of ways. For example, the DNA can be administered by transluminal delivery to the vascular wall, or exoluminally. In another aspect, the active ingredient can be embedded in a biodegradable polymer or sphere and administered by vascular stent. Alternatively, it can be delivered in a pleuronic gel.

Further provided by this invention are methods of inhibiting abnormal smooth muscle cell proliferation in vascular tissue, by introducing into a cell one or more of the ribozymes described above, in an amount effective to inhibit SMC proliferation or abnormal extracellular matrix deposition.

An alternative method of inhibiting abnormal smooth muscle cell proliferation in vascular tissue consists of introducing into a cell an effective amount of DNA encoding a ribozyme described above, under conditions favoring transcription of the DNA to produce the ribozyme. This method also is useful to prevent abnormal SMC and abnormal extracellular matrix deposition and thus prevent restenosis.

Also provided by this invention is a method of inhibiting or preventing abnormal smooth muscle cell proliferation in vascular tissue in a subject (e.g., a warm-blooded animal such as a human) comprising the step of administering to the subject an effective amount of a ribozyme having the ability to inhibit abnormal smooth muscle cell proliferation in vascular tissue. The ribozyme is delivered to the smooth muscle cell exoluminally, transluminally, by stent, by a biodegradable polymer or sphere or in a pleuronic gel.

It should be understood to those skilled in the art that "effective amounts" are administered. These amounts are easily determined using methods well known to those of skill in the art.

The following examples are offered by way of illustration, and not by way of limitation.

EXAMPLES

Example 1

CRITERIA FOR RIBOZYME SITE SELECTION

A. Selection of Sites for Hairpin Ribozymes

Hairpin ribozymes suitable for use within the present invention preferably recognize the following sequence of RNA: NNNBNGUCNNNNNNNN wherein the ribozyme is constructed so as to be complementary to the underlined sequences, and wherein B is C, G or U. The sequence GUC must be conserved for all hairpin ribozymes described below. Other nucleotides ("N" as underlined above) preferably have a high degree of sequence conservation in order to limit the need for multiple ribozymes against the same target site. Representative GUC hairpin ribozyme recognition sites for various genes are provided below in Tables 1–4.

TABLE 1

Hairpin Ribozyme Recognition Sites for cdc 2 kinase

| NUCL. POS. | SEQUENCE (5' to 3') | I.D. No. |
|---|---|---|
| 193 | AGTCAGTCTTCAGGAT | (SEQ ID NO:2) |
| 289 | TCCTGGTCAGTACATG | (SEQ ID NO:3) |
| 530 | CTGGGGTCAGCTCGTT | (SEQ ID NO:4) |

TABLE 2

Hairpin Ribozyme Recognition Sites for Cyclin B1

| NUCL. POS. | SEQUENCE (5' to 3') | I.D. No. |
|---|---|---|
| 12 | TCCGAGTCACCAGGAA | (SEQ ID NO:5) |
| 281 | CCAGTGTCTGAGCCAG | (SEQ ID NO:6) |
| 427 | CCTGTGTCAGGCTTTC | (SEQ ID NO:7) |
| 558 | AAGCAGTCAGACCAAA | (SEQ ID NO:8) |
| 580 | ACTGGGTCGGGAAGTC | (SEQ ID NO:9) |
| 678 | TGACTGTCTCCATTAT | (SEQ ID NO:10) |

TABLE 3

Hairpin Ribozyme Recognition Sites for PCNA

| NUCL. POS. | SEQUENCE (5' to 3') | I.D. No. |
|---|---|---|
| 18 | GCCTGGTCCAGGGCTC | (SEQ ID NO:11) |
| 125 | GACTCGTCCCACGTCT | (SEQ ID NO:12) |

TABLE 3-continued

Hairpin Ribozyme Recognition Sites for PCNA

| NUCL. POS. | SEQUENCE (5' to 3') | I.D. No. |
|---|---|---|
| 158 | CTGCGGTCTGAGGGCT | (SEQ ID NO:13) |
| 867 | TTTCTGTCACCAAATT | (SEQ ID NO:14) |

TABLE 4

Hairpin Ribozyme Recognition Sites for Lysyl Oxidase

| NUCL. POS. | SEQUENCE (5' to 3') | I.D. No. |
|---|---|---|
| 225 | CCGCCGTCCCTGGTGC | (SEQ ID NO:15) |
| 333 | CTGGAGTCACCGCTGG | (SEQ ID NO:16) |
| 364 | CGCCCGTCACTGGTTC | (SEQ ID NO:17) |
| 631 | GTACGGTCTCCCAGAC | (SEQ ID NO:18) |
| 671 | CAGGCGTCCACGTACG | (SEQ ID NO:19) |
| 730 | AAACTGTCTGGCCAGT | (SEQ ID NO:20) |
| 970 | TTTCTGTCTTGAAGAC | (SEQ ID NO:21) |

B. Selection of Cleavage Sites for Hammerhead Ribozymes

Hammerhead ribozymes suitable for use within the present invention preferably recognize the sequence NUX, wherein N is any of G, U, C, or A and X is C, U, or A. Representative hammerhead target sites include:

TABLE 5

Hammerhead Ribozyme Recognition Sites for cdc 2 kinase

| NUCL. POS. | SEQUENCE (5' to 3') | I.D. No. |
|---|---|---|
| 81 | TACAGGTCAAGTGGTA | (SEQ ID NO:22) |
| 159 | AAATTTCTCTATTAAAG | (SEQ ID NO:23) |
| 195 | AGTCAGTCTTCAGGAT | (SEQ ID NO:2) |
| 532 | CTGGGGTCAGCTCGTT | (SEQ ID NO:4) |

TABLE 6

Hammerhead Ribozyme Recognition Sites for Cyclin B1

| NUCL. POS. | SEQUENCE (5' to 3') | I.D. No. |
|---|---|---|
| 14 | TCCGAGTCACCAGGAA | (SEQ ID NO:5) |
| 283 | CCAGTGTCTGAGCCAG | (SEQ ID NO:6) |
| 429 | CCTGTGTCAGGCTTTC | (SEQ ID NO:7) |
| 560 | AACAGTCAGACCAAA | (SEQ ID NO:8) |
| 582 | ACTGGGTCGGGAAGTC | (SEQ ID NO:9) |
| 680 | TGACTGTCTCCATTAT | (SEQ ID NO:10) |

TABLE 7

Hammerhead Ribozyme Recognition Sites for PCNA

| NUCL. POS. | SEQUENCE (5' to 3') | I.D. No. |
|---|---|---|
| 20 | GCCTGGTCCAGGGCTC | (SEQ ID NO:11) |
| 127 | GACTCGTCCCACGTCT | (SEQ ID NO:12) |
| 160 | CTGCGGTCTGAGGGCT | (SEQ ID NO:13) |
| 869 | TTTCTGTCACCAAATT | (SEQ ID NO:14) |

TABLE 8

Hammerhead Ribozyme Recognition Sites for Lysyl Oxidase

| NUCL. POS. | SEQUENCE (5' to 3') | I.D. No. |
|---|---|---|
| 227 | CCGCCGTCCCTGGTGC | (SEQ ID NO:15) |
| 335 | CTGGAGTCACCGCTGG | (SEQ ID NO:16) |
| 366 | CGCCCGTCACTGGTTC | (SEQ ID NO:17) |
| 633 | GTACGGTCTCCCAGAC | (SEQ ID NO:18) |
| 673 | CAGGCGTCCACGTACG | (SEQ ID NO:19) |
| 732 | AAACTGTCTGGCCAGT | (SEQ ID NO:20) |
| 972 | TTTCTGTCTTGAAGAC | (SEQ ID NO:21) |

Example 2

CONSTRUCTION OF HAIRPIN RIBOZYMES

Two single-stranded DNA oligonucleotides are chemically synthesized such that, when combined and converted into double-stranded DNA, they contain the entire hairpin ribozyme, including nucleotides complementary to the target site. In addition, restriction enzyme recognition sites may be placed on either end to facilitate subsequent cloning. More specifically, the oligonucleotides are hybridized together and converted to double-stranded DNA using either Klenow DNA polymerase or Taq DNA polymerase. The resulting DNA is cleaved with restriction enzymes BamHI and MluI, purified and cloned into vectors for in vitro transcription (pGEM, ProMega, Madison, Wis.) or for retrovirus production and mammalian expression (pLNL/MJT backbone). Representative hairpin ribozymes are set forth below (note that the underlined sequences indicate the sites wherein the ribozyme binds the target sequence):

cdc-2 530 (SEQ ID No:24) 5' AACGAGCTAGAA CCAGACCAGAGAAACACACGTTGTGGTATATT-ACCTGGTA 3'

Cyclin B1 281 (SEQ ID No:25) 5' CTGGCTCAAGAA CTGGACCAGAGAAACACACGTTGTGGTATATT-ACCTGGTA 3'

Lysyl Oxidase 333 (SEQ ID No:26) 5' CCAGCGGTAGAA CCAGACCAGAGAAACACACGTTGTGGTATATT-ACCTGGTA 3'

PCNA 158 (SEQ ID No:27) 5' AGCCCTCAAGAA GCAGACCAGAGAAACACACGTTGTGGTATATT-ACCTGGTA 3'

Figure 2:
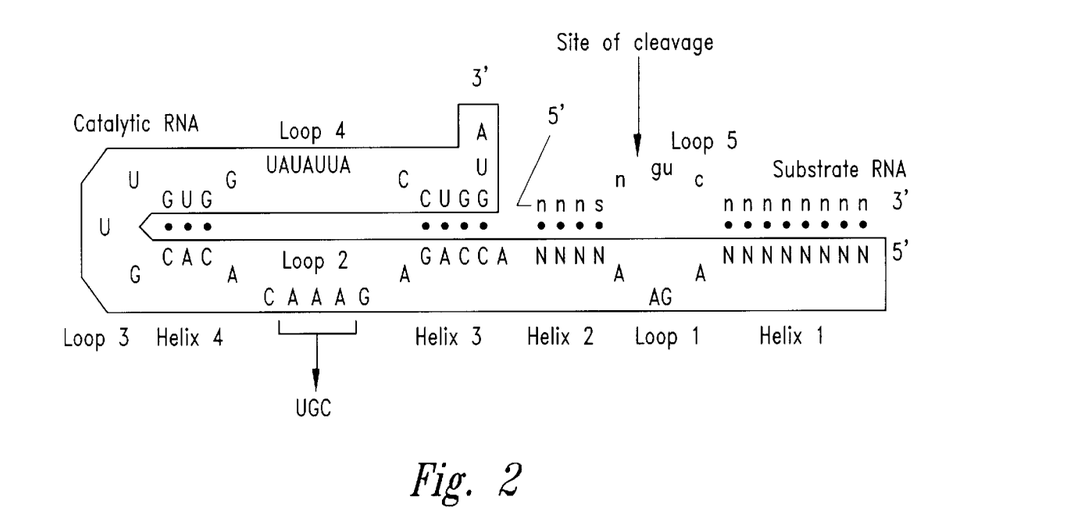
FIG. 2 is a schematic illustration of a representative hairpin ribozyme.

Defective ribozymes for use as controls may be constructed as described above, with the exception that the sequence AAA is changed to a UGC as shown in FIG. 2.

Example 3

CONSTRUCTION OF HAMMERHEAD RIBOZYMES

Figure 5:
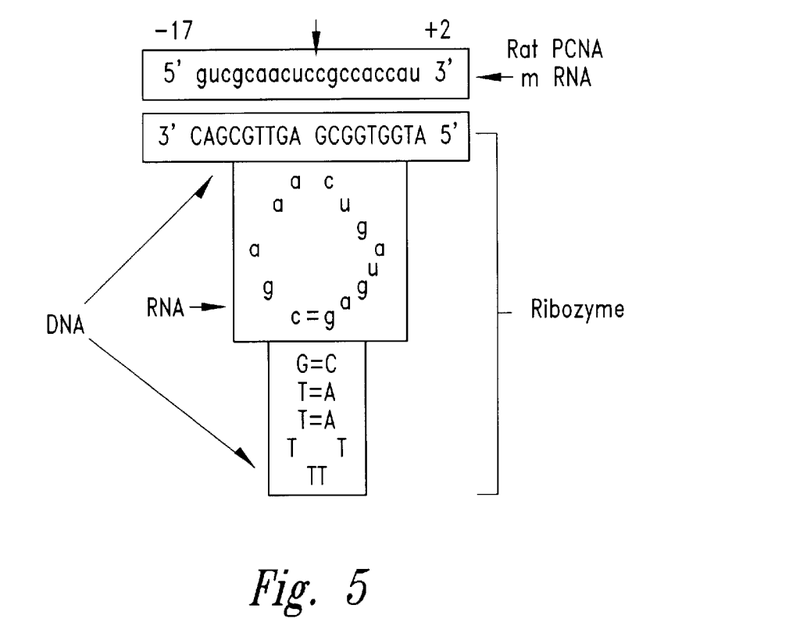
FIG. 5 is a schematic illustration of a ribozyme directed against rat PCNA (SEQ ID NOS: 32 and 33).
Figure 6:
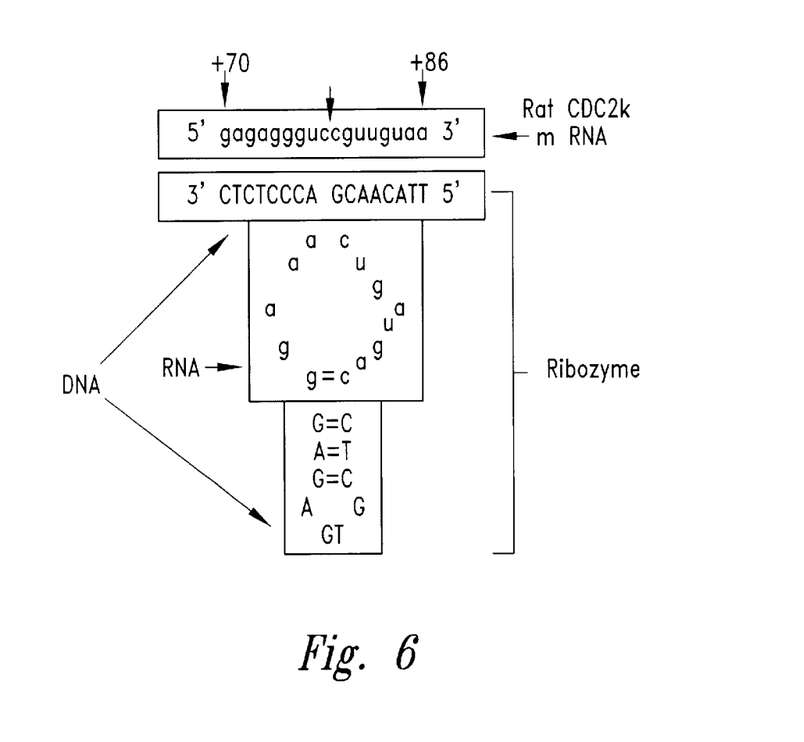
FIG. 6 is a schematic illustration of a ribozyme directed against rat cdc-2 kinase (SEQ ID NOS: 34 and 35).

Chimeric hammerhead ribozymes (i.e., RNA/DNA hybrids) are designed to have an appropriate NUX sequence for ribozyme cleavage. Briefly, ribozymes are chemically synthesized for target sequences of the rat CDC2 kinase gene (nucleotide sequence from −30 to −14), rat PCNA (nucleotide sequence from −17 to +2). (See FIGS. 5 and 6.) In addition, the following human hammerhead ribozymes are synthesized.

cdc-2 532 (SEQ. ID. No:28) 5' AACGAGCTCTGATGACCTCGTGAGAGGGAA ACCCCAG 3'

Cyclin B1 283 (SEQ. ID. No:29) 5' CTGGCTCACTGATGACCTCGTGAGAGGGAA ACACTGG 3'

Lysyl Oxidase 335 (SEQ ID No:30) 5'
CCAGCGGTCTGATGACCTCGTGAGAGGGAA
ACTCCAG 3'

PCNA 160 (SEQ ID No:31) 5'
AGCCCTCACTGATGACCTCGTGAGAGGGAA
ACCGCAG 3'

A scrambled sequence polynucleotide including the same composition of ribonucleotides and deoxyribonucleotides is also synthesized for each ribozyme to serve as a control with no catalytic activity. Lipofectin may be utilized to enhance the uptake of ribozyme into the cells.

Example 4

CONSTRUCTION OF RMBOZYME MAMMALIAN EXPRESSION VECTORS

Figure 1:
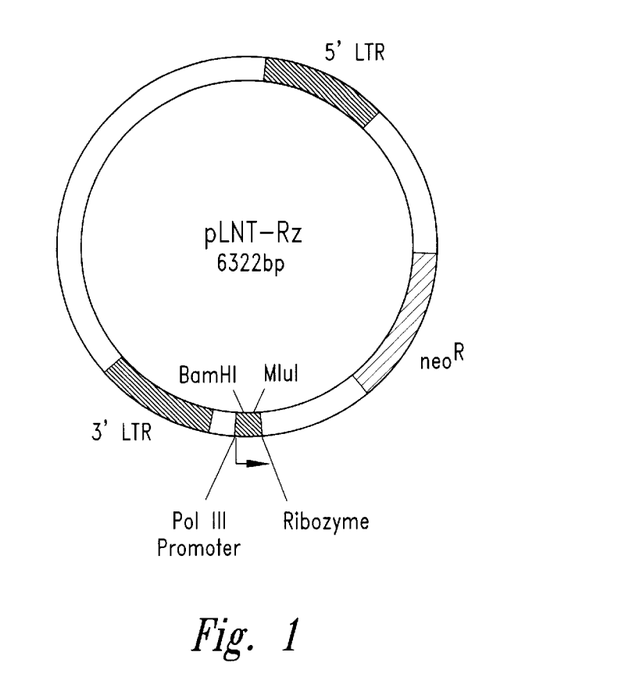
FIG. 1 is a schematic illustration of vector pLNT-Rz.

Plasmid pMJT (Yu et al., Proc. Nat'l Acad. Sci. USA 90:6340–6344, 1993), which contains the anti-U5 HIV ribozyme driven by the tRNA$^{val}$ RNA pol III promoter, is digested with BamHI and MluI, and the vector purified from the ribozyme fragment. The hairpin ribozymes, as described above, are excised from the pGem vector with BamHI and MluI, purified, and ligated into the empty pMJT vector. The resulting vector is designated pLNT-Rz (see FIG. 1), and contains the Moloney LTR driving the neomycin resistance gene and the tRNA$^{val}$ RNA pol III promoter driving expression of the ribozyme.

Example 5

IN VITRO CLEAVAGE ASSAYS

Hairpin ribozymes are cloned into in vitro transcription vectors (pGEM-7Z, ProMega, Madison, Wis.) and transcribed in vitro by T7 RNA polymerase. Following transcription, reactions are treated with DNase and the ribozymes are purified by denaturing polyacrylamide gel electrophoresis. Substrates are then transcribed in vitro in the presence [α-$^{32}$P]UTP and purified by denaturing polyacrylamide gel electrophoresis. The in vitro cleavage reactions are carried out by incubating 40 nM ribozyme with 200 nM substrate at 37° C. for 0 to 60 minutes in 12 mM MgCl2/2 mM spermidine/40 mM Tris-HCl, pH 7.5. Reactions are terminated by the addition of loading buffer (7 M urea/bromophenol blue/xylene cyanol). Products of the cleavage reactions are resolved by electrophoresis on 15% acrylamide/7 M urea gels and analyzed by autoradiography.

Example 6

IN VIVO USE OF RIBOZYMES

A. Experimental Protocol

All animals are treated according to the guidelines of the American Physiological Society. Briefly, a #2 Fr fogarty catheter is used to induce vascular injury in male Sprague-Dawley rats (400 to 500 g in weight). The rats are anesthetized and a cannula is introduced into the left common carotid artery via the external carotid artery. The common carotid artery is then injured by pulling the inflated fogarty catheter through it 3 times. A total of 100 animals are studied and divided into 6 different groups:

TABLE 9

Group 1 (n = 20) balloon injury alone.
Group 2 (n = 15) balloon injury followed by infusion of saline through an isolated segment.

TABLE 9-continued

Group 3 (n = 15) balloon injury followed by local administration of CDC2 kinase ribozyme.
Group 4 (n = 12) balloon injury followed by local delivery of ribozyme to PCNA.
Group 5 (n = 25) balloon injury followed by administration of scrambled sequences of nucleotides resembling CDC2 kinase and PCNA ribozymes.
Group 6 (n + 12) balloon injury followed by local administration of a combination of CDC2 kinase and PCNA ribozymes.

After vessel injury of the common carotid artery, the injured segment is transiently isolated by temporary ligatures. Briefly, two hundred microliters of a combination of lipofectin and hammerhead ribozyme (40 µg) are incubated in the isolated segment for 15 minutes. After the 15 minute incubation, the ligatures are removed. The external carotid artery is ligated and blood flow is restored in the common carotid and the internal carotid artery. The skin wound is then repaired and the animals are transferred to their cages. The animals are then euthanized at 2 weeks and artery is harvested. It s perfusion fixed in formalin and sent for histopathology.

The histopathology sections are then subsequently analyzed by quantitative histology. Using computer facilitated planimetry, the lumen area, area of the intima and area of the media are measured and intimal area to medial area ration is calculated. All values are expressed as mean ± standard deviation and mean ± standard errors of mean. A statistical comparison for each of these parameters is performed between all the groups.

Figure 3:
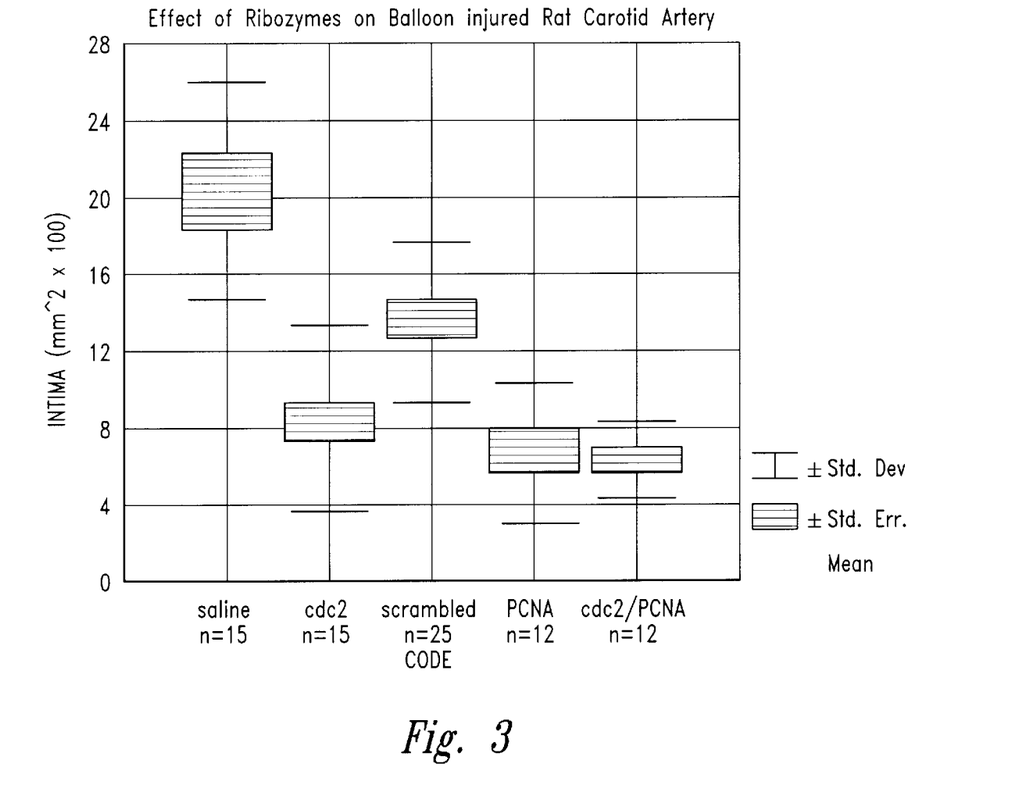
FIG. 3 is a graph which illustrates the effects of ribozymes on a balloon injured rat carotid artery.
Figure 4:
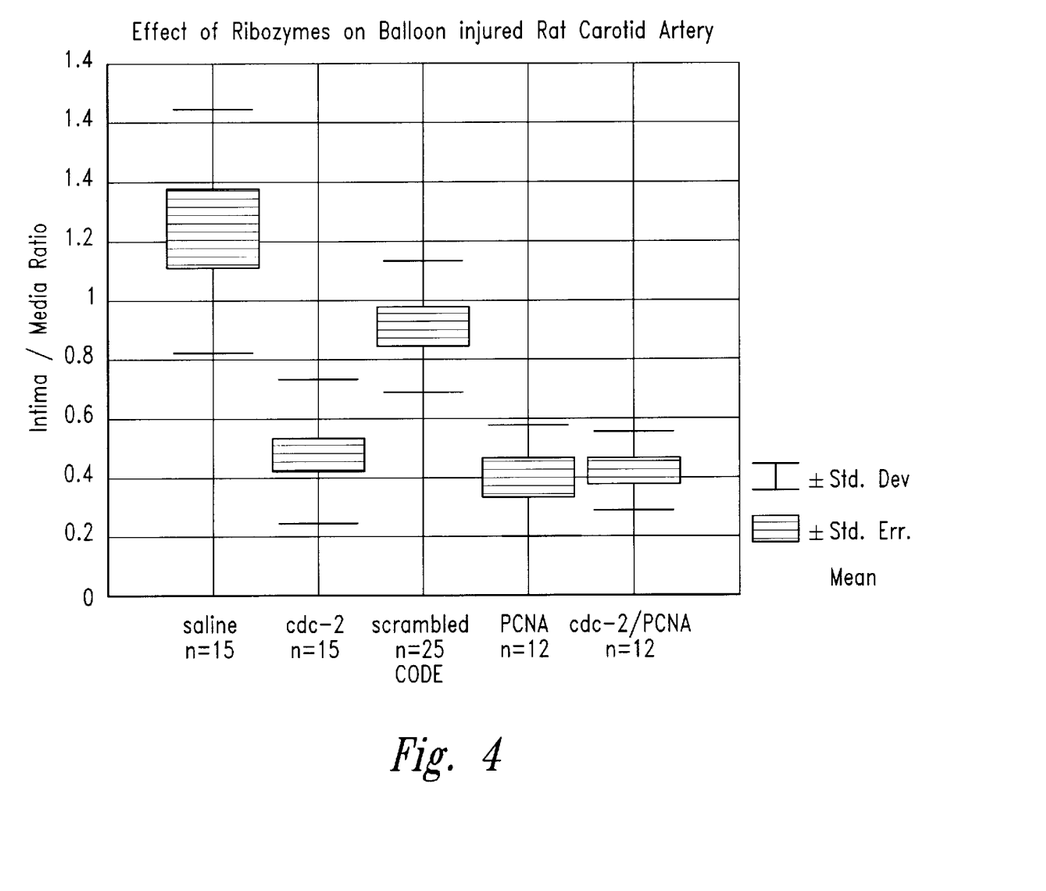
FIG. 4 is a graph which illustrates the effects of ribozymes on a balloon injured rat carotid artery.

Results of the quantitative histology are shown in FIGS. 3 and 4 and summarized in Table 10. Briefly, both the cross-sectional area of the intima and the ratio of the intimal area to medial area were significantly reduced in the ribozyme treated arteries compared with those treated with scrambled-sequence polynucleotides or with normal saline. The intimal hyperplasia was inhibited by the CDC-2 kinase ribozyme, the PCNA ribozyme and their combination. The combination did not seem to have any additive effect.

TABLE 10

| | NO. | | INT | I/M |
|---|---|---|---|---|
| B1 | 14 | MEAN | 13.50 | 0.83 |
| | | STDEV | 4.47 | 0.34 |
| B1 + NS | 8 | MEAN | 17.74 | 1.09 |
| | | STDBV | 6.52 | 0.42 |
| B1 + RZ1 | 18 | MEAN | 8.37 | 0.46 |
| | | STDBV | 5.04 | 0.24 |
| B1 + SCR | 19 | MEAN | 13.24 | 0.92 |
| | | STDEV | 4.43 | 0.26 |
| B1 + RZ2 | 10 | MEAN | 7.21 | 0.43 |
| | | STDEV | 3.87 | 0.24 |
| B1 + RZoom | 10 | MEAN | 6.218783 | 0.41197 |
| | | STDEV | 1.875044 | 0.141841 |

B. Additional Assays
1. Tissue Culture Protocols

Smooth muscle cells (SMC) are isolated from rat aorta and maintained in DMEM medium and 10% FBS. MTT assay: This is a quantitative colorimetric assay for cell proliferation and survival. Rat SMC's (passage 4–8) are seeded into 96 well 10 plate (1500 cells/well) one day before treatment. Cells are then treated with 2 mM of CDC-2 kinase/PCNA ribozyme and 4 mM lipofectin for 1 hour. A second dose of ribozyme (4 mM) is added on day 2. On day 3, 10 mL of MTT is added into each well for 4 hours. The dye in the cells is extracted in DMSO after washing off any supernatant dye from the well. The OD is measured with microplate reader at 590 mM.

The MTT assay using PCNA ribozyme demonstrates significant inhibition of cell proliferation in cell culture as measured by uptake of MTT in comparison to scrambled sequence treated cells and control cells.

2. Quantification of mRNA

SMC's (4–8 passage) are seeded into culture dish one day prior to treatment. RNA is extracted from the cells after treatment with ribozyme, scrambled sequence polynucleotide, 10% FBS or serum free medium for 2 or 6 hours. RT-PCR is then performed utilizing RNA-PCR kit from Perkin Elmer. An appropriated primer sequence for CDC-2 kinase or PCNA is used for analysis. A beta-actin primer is used to ensure that the amount of RNA loaded in each well is approximately equal.

RT-PCR studies using CDC-2 kinase ribozyme show reduction in the CDC-2 kinase MRNA at 2 hours and further reduction at 6 hours in comparison to controls. To ensure that equivalent amount of RNA is loaded in each well, RT-PCR is performed using a primer for beta-actin which shows similar levels of beta-actin mRNA in each group.

3. Protein Expression

Three types of protein assays may also be accomplished, including a) Western blotting; b) Biosynthetic labeling with 35S labeled methionine followed by immunoprecipitation of radiolabelled protein as a measure of newly synthesized target protein; and c) Histone H1 kinase assay for CDC-2 kinase. The Histone H1 kinase assay is a functional assay for CDC-2 kinase and measures the amount of p32 labeled phosphate transferred from ATP to Histone H1.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A hairpin or hammerhead ribozyme which specifically cleaves RNA encoding cdc2-kinase, or PCNA.

2. A nucleic acid molecule encoding the ribozyme of claim 1.

3. The nucleic acid molecule of claim 2, wherein the nucleic acid is DNA or cDNA.

4. The nucleic acid molecule of claim 2, under the control of a promoter to transcribe the nucleic acid.

5. A host cell comprising the ribozyme of claim 1.

6. A vector comprising the nucleic acid of claim 2.

7. A host cell comprising the vector of claim 6.

8. The vector of claim 6, wherein the vector is a plasmid, a virus, retrotransposon or a cosmid.

9. The vector of claim 8, wherein the vector is an adenoviral vector or an AAV.

10. A host cell stably transformed with the vector of claim 9.

11. The host cell of claim 5 or 10, wherein the host cell is a human cell.

12. A method for producing a ribozyme, comprising transcribing the nucleic acid molecule according to claim 4.

13. The method of claim 12, wherein the ribozyme is produced in vitro.

14. The method of claim 13, further comprising purifying the ribozyme produced.

15. The method of claim 12, wherein the ribozyme is produced in vivo.

16. A method of inhibiting abnormal smooth muscle cell proliferation in vascular tissue, comprising introducing into a cell an effective amount of the ribozyme of claim 1.

17. A method of inhibiting abnormal smooth muscle cell proliferation in vascular tissue, which comprises introducing into a cell an effective amount of the DNA of claim 4 under conditions favoring transcription of the DNA to produce the ribozyme.

18. The method of claim 16 or 17, wherein said cell is a human vascular smooth muscle cell.

19. A method of inhibiting restenosis, comprising introducing into a cell an effective amount of the DNA of claim 4 under conditions favoring transcription of the DNA to produce the ribozyme.

20. The method of claim 19, wherein said cell is a human vascular smooth muscle cell.

21. A method of inhibiting or preventing abnormal smooth muscle cell proliferation in vascular tissue in a subject, which comprises administering to the subject an effective amount of the ribozyme of claim 1.

22. The method of claim 21, wherein the ribozyme is delivered to the smooth muscle cell exoluminally, transluminally, by stent, by a biodegradable polymer or sphere or in a pleuronic gel.

* * * * *

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( x i ) SEQUENCE DESCRIPTION: SEQ ID NO:1:

NNNBNGUCNN NNNNNN 16

( 2 ) INFORMATION FOR SEQ ID NO:2:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( x i ) SEQUENCE DESCRIPTION: SEQ ID NO:2:

AGTCAGTCTT CAGGAT 16

( 2 ) INFORMATION FOR SEQ ID NO:3:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( x i ) SEQUENCE DESCRIPTION: SEQ ID NO:3:

TCCTGGTCAG TACATG 16

( 2 ) INFORMATION FOR SEQ ID NO:4:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( x i ) SEQUENCE DESCRIPTION: SEQ ID NO:4:

CTGGGGTCAG CTCGTT                                                                                       16

( 2 ) INFORMATION FOR SEQ ID NO:5:

( i ) SEQUENCE CHARACTERISTICS:
　　　　　　　　( A ) LENGTH: 16 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:5:

TCCGAGTCAC CAGGAA                                                                                       16

( 2 ) INFORMATION FOR SEQ ID NO:6:

( i ) SEQUENCE CHARACTERISTICS:
　　　　　　　　( A ) LENGTH: 16 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:6:

CCAGTGTCTG AGCCAG                                                                                       16

( 2 ) INFORMATION FOR SEQ ID NO:7:

( i ) SEQUENCE CHARACTERISTICS:
　　　　　　　　( A ) LENGTH: 16 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:7:

CCTGTGTCAG GCTTTC                                                                                       16

( 2 ) INFORMATION FOR SEQ ID NO:8:

( i ) SEQUENCE CHARACTERISTICS:
　　　　　　　　( A ) LENGTH: 16 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:8:

AAGCAGTCAG ACCAAA                                                                                       16

( 2 ) INFORMATION FOR SEQ ID NO:9:

( i ) SEQUENCE CHARACTERISTICS:
　　　　　　　　( A ) LENGTH: 16 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:9:

ACTGGGTCGG GAAGTC                                                                                       16

( 2 ) INFORMATION FOR SEQ ID NO:10:

( i ) SEQUENCE CHARACTERISTICS:
　　　　　　　　( A ) LENGTH: 16 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:10:

TGACTGTCTC CATTAT 16

( 2 ) INFORMATION FOR SEQ ID NO:11:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:11:

GCCTGGTCCA GGGCTC 16

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:12:

GACTCGTCCC ACGTCT 16

( 2 ) INFORMATION FOR SEQ ID NO:13:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:13:

CTGCGGTCTG AGGGCT 16

( 2 ) INFORMATION FOR SEQ ID NO:14:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:14:

TTTCTGTCAC CAAATT 16

( 2 ) INFORMATION FOR SEQ ID NO:15:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:15:

CCGCCGTCCC TGGTGC 16

( 2 ) INFORMATION FOR SEQ ID NO:16:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:16:

CTGGAGTCAC CGCTGG 16

( 2 ) INFORMATION FOR SEQ ID NO:17:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:17:

CGCCCGTCAC TGGTTC                                   16

( 2 ) INFORMATION FOR SEQ ID NO:18:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:18:

GTACGGTCTC CCAGAC                                   16

( 2 ) INFORMATION FOR SEQ ID NO:19:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:19:

CAGGCGTCCA CGTACG                                   16

( 2 ) INFORMATION FOR SEQ ID NO:20:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:20:

AAACTGTCTG GCCAGT                                   16

( 2 ) INFORMATION FOR SEQ ID NO:21:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:21:

TTTCTGTCTT GAAGAC                                   16

( 2 ) INFORMATION FOR SEQ ID NO:22:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:22:

TACAGGTCAA GTGGTA                                   16

( 2 ) INFORMATION FOR SEQ ID NO:23:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

AAATTTCTCT ATTAAAG                                                                                      17

( 2 ) INFORMATION FOR SEQ ID NO:24:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

AACGAGCTAG AACCAGACCA GAGAAACACA CGTTGTGGTA TATTACCTGG TA                                                52

( 2 ) INFORMATION FOR SEQ ID NO:25:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

CTGGCTCAAG AACTGGACCA GAGAAACACA CGTTGTGGTA TATTACCTGG TA                                                52

( 2 ) INFORMATION FOR SEQ ID NO:26:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

CCAGCGGTAG AACCAGACCA GAGAAACACA CGTTGTGGTA TATTACCTGG TA                                                52

( 2 ) INFORMATION FOR SEQ ID NO:27:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

AGCCCTCAAG AAGCAGACCA GAGAAACACA CGTTGTGGTA TATTACCTGG TA                                                52

( 2 ) INFORMATION FOR SEQ ID NO:28:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

AACGAGCTCT GATGACCTCG TGAGAGGGAA ACCCCAG                                                                 37

( 2 ) INFORMATION FOR SEQ ID NO:29:

( i ) SEQUENCE CHARACTERISTICS:

( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

CTGGCTCACT GATGACCTCG TGAGAGGGAA ACACTGG 37

( 2 ) INFORMATION FOR SEQ ID NO:30:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

CCAGCGGTCT GATGACCTCG TGAGAGGGAA ACTCCAG 37

( 2 ) INFORMATION FOR SEQ ID NO:31:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

AGCCCTCACT GATGACCTCG TGAGAGGGAA ACCGCAG 37

( 2 ) INFORMATION FOR SEQ ID NO:32:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

GUCGCAACUC CGCCACCAU 19

( 2 ) INFORMATION FOR SEQ ID NO:33:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

CAGCGTTGAA AAGCGTTTTT TAACGAGUAG UCGCGGTGGT A 41

( 2 ) INFORMATION FOR SEQ ID NO:34:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

GAGAGGGUCC GUUGUAA 17

( 2 ) INFORMATION FOR SEQ ID NO:35:

( i ) SEQUENCE CHARACTERISTICS:
        ( A ) LENGTH: 38 base pairs
        ( B ) TYPE: nucleic acid -continued (C) STRANDEDNESS: single
(D) TOPOLOGY: linear (xi) SEQUENCE DESCRIPTION: SEQ ID NO:35:

CTCTCCCAAA GGGAGAGTGC TCCAGUAGUC GCAACATT    38